(12) United States Patent
Kajiyama et al.

(10) Patent No.: US 7,074,428 B2
(45) Date of Patent: *Jul. 11, 2006

(54) QUICK DISINTEGRATING TABLET IN BUCCAL CAVITY AND MANUFACTURING METHOD THEREOF

(75) Inventors: Atushi Kajiyama, Shizuoka (JP); Tetsuya Tamura, Shizuoka (JP); Takao Mizumoto, Shizuoka (JP); Hitoshi Kawai, Shizuoka (JP); Tatsuya Takahashi, Shizuoka (JP)

(73) Assignee: Astellas Pharma Inc., Tokyo (JP)

( * ) Notice: Subject to any disclaimer, the term of this patent is extended or adjusted under 35 U.S.C. 154(b) by 341 days.

This patent is subject to a terminal disclaimer.

(21) Appl. No.: 10/667,077

(22) Filed: Sep. 18, 2003

(65) Prior Publication Data

US 2004/0071773 A1   Apr. 15, 2004

Related U.S. Application Data

(63) Continuation of application No. 09/896,820, filed on Jun. 28, 2001, now Pat. No. 6,656,492.

(60) Provisional application No. 60/215,292, filed on Jun. 30, 2000.

(51) Int. Cl.
*A61K 9/20* (2006.01)
*A61K 9/28* (2006.01)
*A61K 9/14* (2006.01)
*A61K 9/16* (2006.01)

(52) U.S. Cl. ............ 424/464; 424/465; 424/474; 424/489; 424/490

(58) Field of Classification Search ........ 424/434, 424/435, 464, 484, 489, 490, 465, 474; 427/446
See application file for complete search history.

(56) References Cited

U.S. PATENT DOCUMENTS 4,760,094 A    7/1988  Blank et al.
4,835,188 A    5/1989  Ho et al.
5,851,553 A *  12/1998 Myers et al.
6,316,029 B1 * 11/2001 Jain et al.

FOREIGN PATENT DOCUMENTS

| EP | 0257310 | 2/1988 |
|---|---|---|
| EP | 0267702 A2 | 5/1988 |
| EP | 0322137 A1 | 6/1989 |
| EP | 0553777 A2 | 8/1993 |
| EP | 0 745 382 | * 12/1996 |
| EP | 0745382 A1 | 12/1996 |
| EP | 0998921 A1 | 5/2000 |
| EP | 1072256 A1 | 1/2001 |
| JP | 49-133513 A | 12/1974 |
| JP | 8-291051 A | 11/1996 |
| JP | 2000-86537 A | 3/2000 |
| JP | 2000169364 | 6/2000 |
| WO | WO 00/18372 | 4/2000 |
| WO | WO 00/18372 A1 | 4/2000 |

* cited by examiner

*Primary Examiner*—Humera N. Sheikh
(74) *Attorney, Agent, or Firm*—Townsend and Townsend and Crew LLP

(57) ABSTRACT

The present invention pertains to a quick disintegrating tablet in buccal cavity, characterized in that drug-containing particles with a mean particle diameter of approximately 50 to approximately 250 μm and an apparent specific gravity of approximately 0.5 to approximately 1.2 consisting of a bitter tasting drug and/or drug of inferior fluidity and a pharmaceutical preparation carrier and obtained by spray drying are added to a quick disintegrating tablet in buccal cavity comprising a drug and a saccharide. Moreover, the present invention pertains to a method for manufacturing drug-containing particles having a specific mean particle diameter and specific apparent gravity by dissolving and suspending a bitter tasting drug and/or drug of inferior fluidity and a pharmaceutical preparation carrier to a high concentration in terms of solid concentration in a solvent and spray drying this liquid and a method for manufacturing a quick disintegrating tablet in buccal cavity comprising the particles.

17 Claims, No Drawings

QUICK DISINTEGRATING TABLET IN BUCCAL CAVITY AND MANUFACTURING METHOD THEREOF

CROSS-REFERENCE TO RELATED APPLICATIONS

This application is a continuation of U.S. patent application Ser. No. 09/896,820, filed Jun. 28, 2001, now U.S. Pat. No. 6,656,492, which application claims priority to U.S. Provisional Patent Application No. 60/215,292, filed Jun. 30, 2000, which is hereby incorporated by reference in its entirety for all purposes.

FIELD OF THE INVENTION

The present invention pertains to a quick disintegrating tablet in buccal cavity, characterized in that drug-containing particles with a mean particle diameter of approximately 50~approximately 250 µm (preferably approximately 50 to approximately 150 µm) and an apparent specific gravity of approximately 0.5~approximately 1.2 (preferably approximately 0.5 to approximately 1) consisting of a bitter tasting drug and/or a drug of inferior fluidity and a pharmaceutical preparation carrier and obtained by spray drying are added to a quick disintegrating tablet in buccal cavity comprising drug and saccharide. Moreover, the present invention pertains to a method of manufacturing a quick disintegrating tablet in buccal cavity comprising a drug and saccharide consisting of (a) the process whereby a bitter tasting drug and/or a drug of inferior fluidity and a pharmaceutical preparation carrier are dissolved and suspended to approximately 30~approximately 70 w/w % in terms of solid concentration in a solvent that is pharmaceutically acceptable to prepare the suspension for spray drying, (b) the process whereby the suspension obtained by process (a) is spray dried using a rotating disk-type spray dryer, with the rotating speed of the disk being approximately 5,000~approximately 15,000 rpm, in order to prepare drug-containing particles, and (c) the process whereby the drug-containing particles obtained by process (b) and a saccharide are mixed and this mixture is molded.

DESCRIPTION OF THE RELATED ART

Various disintegrating tablets in buccal cavity have been developed in recent years which can be taken by elderly people and children without water. An invention pertaining to a compression molding that dissolves in the buccal cavity, which is obtained by granulation of saccharide of low moldability with saccharide of high moldability and then compression molding of this granulation product (hereafter also abbreviated as saccharide modification method) is disclosed in World Early Disclosure Pamphlet WO 95/20380 (corresponds to U.S. Pat. No. 5,576,014). This invention is characterized in that a solution of a saccharide of high moldability is used as the binder and this is sprayed and granulated or coated on the saccharide of low moldability for saccharide modification. It is also disclosed in this patent that moistening and drying should be performed after compression molding in order to further improve tablet strength. Lactose, mannitol, glucose, sucrose, xylitol, etc., are disclosed as saccharides of low moldability and maltose, maltitol, sorbitol, lactosucrose, etc., are disclosed as saccharides of high moldability in this invention.

Moreover, an invention pertaining to a disintegrating tablet in buccal cavity that comprises a drug, saccharide and amorphous saccharide and that is obtained by molding and then moistening and drying is disclosed in World Early Disclosure Pamphlet WO 99/47124 (corresponds to European Patent No. EP 1,072,256). This invention is characterized in that in order to bind the tablet starting materials, such as drug, saccharide, etc., the tablet starting materials are molded using saccharide that can be converted to an amorphous substance and then this molding is moistened and dried to obtain a quick disintegrating tablet in buccal cavity (hereafter also referred to as amorphous saccharide moistening and drying method). That is, this invention is characterized in that by using this structure, saccharide that can be converted to an amorphous substance is converted to an amorphous substance and then crystallization occurs within the tablet so that tablet strength is improved. Mannitol, maltitol, erythritol, xylitol, etc., are disclosed as the saccharide (crystalline saccharide) in this case, while lactose, sucrose, glucose, sorbitol, maltose, trehalose, lactitol, fructose, etc., are disclosed as saccharides that can be converted to an amorphous substance (saccharides that are crystallized by moistening and drying after conversion to an amorphous substance). These saccharide modification method and amorphous saccharide moistening and drying method are excellent methods in that compression moldings that dissolve in the buccal cavity with the ability to be quickly disintegrated and dissolved in the buccal cavity and with enough strength be handled as a pharmaceutical preparation are presented by a manufacturing method that is excellent in terms of industrial productivity.

Nevertheless, there is no record of mixing drug-containing particles with a specific mean particle diameter and specific apparent specific gravity that are obtained by spray drying in the Specifications in which the above-mentioned saccharide modification method or amorphous saccharide moistening and drying method are disclosed, and when bitter tasting drug of inferior fluidity (for instance, drug that has needle-shaped crystal and therefore is of inferior fluidity), or bitter tasting drug, is used in the quick disintegrating tablet in buccal cavity by the above-mentioned methods, satisfactory results are not obtained in that it is impossible to thoroughly mask the bitter taste and fluidity cannot be improved satisfactorily and therefore, there is a marked reduction in productivity, etc.

On the other hand, the following methods are known as technology for making bitter tasting drugs tasteless by spray drying: An invention pertaining to ibuprofen powder obtained by spray drying a liquid of ibuprofen, ethyl cellulose, and plasticizer suspended in water using a spray dryer is disclosed in U.S. Pat. No. 4,835,188. Moreover, an invention pertaining to acetaminophen powder obtained by spray drying a liquid of acetaminophen, ethyl cellulose, and plasticizer in water using a spray dryer is disclosed in U.S. Pat. No. 4,760,094.

The particle diameter of the powders obtained by these methods is not disclosed in these texts. Nevertheless, only the invention involving preparation with a spray dryer having a rotating disk with which the rotating speed of the disk is controlled by variable air pressure is specifically disclosed in the Specifications of these texts, and since it is usually necessary to turn the rotating disk at 30,000 to 20,000 rpm with this device, it is estimated that powders manufactured with this device usually have a mean particle diameter of 30 µm or smaller. The fact that particle diameter becomes smaller when the same amount of drug is used in these inventions indicates that surface area increases because there is an increase in the number of particles themselves and bitter taste cannot be thoroughly hidden, depending on the extent of the bitter taste of the drug. Moreover, even if a large particle diameter can be obtained, only hollow particles can be made if the solid concentration of the aqueous suspension for spray drying is low and therefore, for the same reason as mentioned above, there would be an increase in surface area and it would not be possible to thoroughly cover the bitter taste of the drug.

Consequently, drug-containing particles consisting of a bitter tasting drug of inferior fluidity, a bitter tasting drug, or a drug of inferior fluidity and a pharmaceutical preparation carrier having a specific mean particle diameter and specific apparent specific gravity obtained by spray drying are not specifically disclosed in either of the above-mentioned texts.

On the other hand, the granulation method is a well-known technology for improving drug fluidity. Nevertheless, it is not possible to thoroughly hide the bitter taste and simultaneously improve the fluidity of, for instance, bitter tasting drugs with needle-shaped crystal by the above-mentioned method (refer to Summary of the Invention and description of famotidine that follow). Moreover, it is difficult to manufacture a quick disintegrating tablet in buccal cavity that simultaneously has both sufficient tablet strength to be handled as a pharmaceutical preparation and the ability to disintegrate and dissolve quickly in the buccal cavity when a drug that does not pose a problem in terms of bitter taste, but is of inferior fluidity is used in large amounts (drug exceeds 40 wt % of the pharmaceutical preparation weight), even if the drug is granulated with a conventional medical filler and a quick disintegrating tablet in buccal cavity consisting of this granulation product is prepared.

BRIEF SUMMARY OF THE INVENTION

When they studied the use of famotidine, which has a bitter taste, in tablets that disintegrate in the buccal cavity, the inventors found that there are problems in that (1) because famotidine is a drug with needle-shaped crystal, large amounts of masking agent are needed to mask the bitter taste, but when large amounts of masking agent are used, there is a reduction in bioavailability, (2) when famotidine is coated by a masking agent in a fluidized bed granulating machine that is normally used for manufacture in above-mentioned (1), uniform fluidity cannot be obtained, making the coating procedure difficult, because fluidity of the famotidine is inferior, (3) it is necessary to increase the coated article particle diameter in order to alleviate the bitter taste of famotidine by simultaneously coating with masking agent and granulating the famotidine and therefore, a gritty feeling and feeling of extraneous matter remain in the buccal cavity, (4) when the famotidine is coated with masking agent in the fluidized bed granulating machine, granulation product is manufactured with the famotidine in the form of needle-shaped crystals and therefore, there will be cases where the granulation product is crushed by tableting pressure when it is being made into tablets that disintegrate in the buccal cavity with a tableting machine and as a result, drug elution is promoted and a bitter taste is presented, etc.

The inventors knew as a result of performing intense studies under these conditions that if famotidine, which is a bitter tasting drug with needle-shaped crystal and therefore of inferior fluidity, is crushed to smaller than a specific size and dissolved and suspended with masking agent (pharmaceutical preparation carrier) in a solvent to a high concentration that is not normally used in terms of solid concentration and then this suspension is spray dried using a spray dryer, famotidine-containing particles having a specific average particle diameter and a specific apparent specific gravity are obtained with which the bitter taste of the famotidine is controlled and fluidity of famotidine, which is of inferior fluidity owing to its needle-shaped crystal, is improved. As a result of continuing with further research, the inventors successfully completed the present invention upon clarifying that a bitter tasting drug of inferior fluidity, as well as bitter tasting drug or drug of inferior fluidity, can be used.

That is, the present invention presents

1. A quick disintegrating tablet in buccal cavity, said quick disintegrating tablet comprising:
   a) a plurality of drug-containing particles, wherein each particle comprises a bitter tasting drug and/or a drug of inferior fluidity and a pharmaceutical preparation carrier, wherein each particle has a mean diameter of approximately 50 to approximately 250 μm and an apparent specific gravity of approximately 0.5 to approximately 1.2; and
   b) a saccharide.
2. The quick disintegrating tablet in buccal cavity of claim 1, wherein the drug of inferior fluidity has an angle of repose of 41°~90°.
3. The quick disintegrating tablet in buccal cavity of claim 1, wherein the pharmaceutical preparation carrier is 1 or 2 or more selected from the group consisting of water-insoluble polymers, gastrosoluble polymers, enterosoluble polymers, wax-like substances and saccharides.
4. The quick disintegrating tablet in buccal cavity of claim 3, wherein the pharmaceutical preparation carrier is a water-insoluble polymer.
5. The quick disintegrating tablet in buccal cavity of claim 4, wherein the water-insoluble polymer is a water-insoluble cellulose ether or a water-insoluble acrylic acid copolymer.
6. The quick disintegrating tablet in buccal cavity of claim 1, wherein the amount of pharmaceutical preparation carrier added is about 0.05 to about 3 parts by weight per 1 part by weight bitter tasting drug and/or drug of inferior fluidity.
7. The quick disintegrating tablet in buccal cavity of claim 1, wherein the saccharide is a granulation product obtained by spraying to coat and/or granulate a saccharide of low moldability using a saccharide of high moldability as a binder.
8. The quick disintegrating tablet in buccal cavity of claim 7, wherein the saccharide of low moldability is 1 or 2 or more selected from the group consisting of lactose, mannitol, glucose, sucrose, xylitol, and erythritol.
9. The quick disintegrating tablet in buccal cavity of claim 7, wherein the saccharide of high moldability is 1 or 2 or more selected from the group consisting of maltose, maltitol, sorbitol, trehalose, and lactosucrose.
10. The quick disintegrating tablet in buccal cavity of claim 1, wherein the mean particle diameter of the plurality of drug-containing particles is approximately 50 μm to approximately 150 μm.
11. The quick disintegrating tablet in buccal cavity of claim 1, wherein the apparent specific gravity of the plurality of drug-containing particles is approximately 0.5~approximately 1.
12. A drug-containing particle, wherein said drug containing particle has a mean particle diameter of approximately 50 to approximately 250 μm and an apparent specific gravity of approximately 0.5 to approximately 1.2, and comprises a bitter tasting drug and a water-insoluble polymer.
13. A drug-containing particle, wherein said drug containing particle has a mean particle diameter of approximately 50 to approximately 250 μm and an apparent specific gravity of approximately 0.5 to approximately 1.2, and comprises a drug of inferior fluidity and a saccharide.

14. A method for manufacturing a quick disintegrating tablet in buccal cavity, said quick disintegrating tablet comprising a drug and a saccharide, said method comprising the steps of:
(a) dissolving a bitter tasting drug and/or a drug of inferior fluidity and a pharmaceutical preparation carrier to form a mixture that is dissolved and suspended to approximately 30 to approximately 70 w/w % in terms of solid concentration in a solvent that is pharmaceutically acceptable to prepare a suspension for spray drying;
(b) spray drying said suspension using a rotating disk-type spray dryer, with the disk rotating at a speed of approximately 5,000 to approximately 15,000 rpm to prepare the drug-containing particles; and
(c) mixing the drug-containing particles with a saccharide to form a mixture that is molded.

15. The method for manufacturing a quick disintegrating tablet in buccal cavity of claim 14, wherein said saccharide is a granulation product obtained by spraying to coat and/or granulate a saccharide of low moldability using a saccharide of high moldability as a binder.

16. A method for manufacturing a quick disintegrating tablet in buccal cavity of claim 14, wherein (d) the process of moistening and drying is further performed in succession to process (c) on the molding obtained under at least the pressure needed to retain tablet form.

17. The method for manufacturing a quick disintegrating tablet in buccal cavity of claim 14, wherein the solid concentration in step (a) is approximately 40 to approximately 70 w/w %.

18. The method for manufacturing a quick disintegrating tablet in buccal cavity of claim 14, wherein the rotating speed of the rotating disk in process (b) is approximately 6,000 to approximately 12,000 rpm.

19. The method for manufacturing a quick disintegrating tablet in buccal cavity of claim 14, wherein a bitter tasting drug and/or a drug of inferior fluidity whose particle diameter has been brought to approximately 5 to approximately 100 μm is used in process (a).

20. A quick disintegrating tablet in buccal cavity, which is manufactured by the method of claim 14.

The "quick disintegrating tablet in buccal cavity" in the present invention means a tablet that is disintegrated in the buccal cavity within 1 minute by essentially saliva only without taking water for swallowing tablets.

The quick disintegrating tablet in buccal cavity of the present invention will now be described:

The characterizing points of the quick disintegrating tablet of the present invention are (1) a bitter tasting drug and/or drug of inferior fluidity and a pharmaceutical preparation carrier (preferably containing water-insoluble polymer, particularly at least aqueous ethyl cellulose suspension (preferably containing plasticizer)) are dissolved and suspended to a high concentration (approximately 30~approximately 70 w/w %, preferably approximately 40~approximately 70 w/w %, particularly approximately 50~approximately 65 w/w %) in terms of solid concentration in a solvent that is pharmaceutically acceptable, (2) drug-containing particles manufactured by spray drying this suspension using a rotating disk-type spray dryer, with the disk operating at low speed (approximately 5,000~approximately 15,000 rpm, preferably approximately 6,000 to approximately 12,000 rpm), are added, and (3) the drug-containing particles have a specific mean particle diameter (approximately 50~250 μm, preferably approximately 50~approximately 150 μm) and a specific apparent specific gravity (approximately 0.5~approximately 1.2, preferably approximately 0.5 to approximately 1). Moreover, the above-mentioned drug-containing particles have excellent effects in that they alleviate the bitter taste of bitter tasting drugs, improve fluidity of drugs of inferior fluidity (particularly drugs with needle-shaped crystal), or they alleviate the bitter taste of and improve the fluidity of bitter-tasting drugs of inferior fluidity, and thereby thoroughly mask bitter taste, they have the ability to quickly disintegrate and dissolve in the buccal cavity, and they have the tablet strength needed for good industrial productivity and handling as a quick disintegrating tablet in buccal cavity comprising these drug-containing particles.

The "mean particle diameter" of the present specification means cumulative 50% mean particle diameter of the powder particles (mean diameter in terms of weight). Said mean particle diameter can be found by determination after selecting the appropriate size mesh (22 to 325 mesh) in 8 set steps using, for instance, an ultrasonic shaking-type fully automated sieving particle diameter distribution equipment, which is a dry sieving meter (Seishin Industries, Robot Sifter).

The "apparent specific gravity" in the present specification means the ratio of the mass of the powder and the volume it occupies when filled in a container (after tapping). A smaller apparent specific gravity indicates that the particles are hollow or porous. Said apparent specific gravity can be found from powder weight (g) per 1 $cm^3$ when tapping has been performed a specific number of times (180 times for 3 minutes) using a packed apparent specific gravity determination machine (Hosokawa Micron Corp., Powder Tester).

There are no special restrictions to the bitter tasting drug used in the present invention as long as it is one that is used for treatment or prevention of disease as a pharmaceutically active component and it is one with a bitter or unpleasant taste. There are no special restrictions to the drug of inferior fluidity used in the present invention as long as it is one that is used for treatment or prevention of disease as a pharmaceutically active component and is the cause of tableting errors during the tablet-making process because of inferior fluidity. In addition to being identified by their angle of repose (refer to later in the text), for instance, drugs "of inferior fluidity" can have a crystal shape that is, for instance, needle-shaped crystal, or they can be drugs that are powders with a powder diameter of 50 μm or smaller and generate electrostatic aggregation, etc. The angle of repose is usually 41~90° C., preferably 46~90°. Said drugs are preferably ones that are bitter tasting and of inferior fluidity, or ones that are bitter tasting, further, ones that are bitter tasting and of inferior fluidity, particularly ones that are bitter tasting and of inferior fluidity owing to needle-shaped crystal or plate crystal. Examples of this drug are hypnotic sedatives, sleep-inducing agents, anti-anxiety drugs, anti-epilepsy drugs, antidepressants, anti-Parkinson's drugs, psychoneurotic drugs, central nervous system drugs, local anesthetics, skeletal muscle relaxants, autonomic nerve drugs, antipyretic analgesic anti-inflammatory agents, antispasmotics, anti-vertigo drugs, cardiotonics, drugs for arrhythmia, diuretics, hypotensives, vasoconstrictors, vasodilators, drugs for the circulatory system, drugs for hyperlipidemia, drugs to promote respiration, antitussives, expectorants, antitussive expectorants, bronchodilators, antidiarrheal agents, drugs for controlling intestinal function, drugs for peptic ulcer, stomachics, antacids, laxatives, cholagogues, gastrointestinal drugs, adrenocortical hormones, hormones, urogenital drugs, vitamins, hemostatics, drugs for liver disease, drugs used for gout, drugs used for diabetes, antihistamines, antibiotics, antibacterials, drugs used against malignant tumors, chemotherapeutic drugs, multisymptom cold medications, nutrition-enhancing health drugs, osteoporosis drugs, etc. For instance, acetominophen, meclofenoxate hydrochloride, chloramphenicol, aminophylline, erythromycin, josamycin, indeloxazine hydrochloride, calcium homopantothenate, phenobarbital, cimetidine, ranitidine, famotidine, etilefrin hydrochloride, diltiazem hydrochloride, propranolol hydrochloride, flufenamic acid, digitoxin, theophylline, promethazine hydrochloride, quinine hydrochloride, sulpyrin, ibuprofen, ambroxol, calcium carbonate, etc., are given. One or a combination of two or more drugs can be used. There are no special restrictions to the amount of drug that is added as long as it is the effective dose in terms of treating or preventing disease, but it is usually 50 wt/wt % or less, preferably 20 wt/wt % or less, of the total preparation. If the particle diameter of the spray dried drug-containing particles is large, it will be the source of a gritty feeling when it disintegrates in the mouth and therefore, mean particle diameter should be 250 μm or smaller. Consequently, if mean particle diameter of the drug is greater than 250 μm, it is preferred that the drug usually be pre-crushed to a size of a mean particle diameter of approximately 1~approximately 200 μm, preferably pre-crushed to a size of a mean particle diameter of approximately 5~approximately 100 μm, particularly pre-crushed to a size of approximately 5~approximately 30 μm, using an appropriate crushing machine, such as a hammer mill, sample mill, jet mill, etc.

The term "fluidity" in the present Specification means adhesion and cohesion between particles or adhesion of a particle with a solid wall surface. Said "fluidity" can be put into numerical terms by, for instance, methods of determining the angle of repose of a powder. Methods of determining the angle of repose are known to those in the field, but the fixed base cone method by funnel is an example (for instance, "Yakuzaigaku," Ryuichi Arita, Hitoshi Sezaki, editors (Kodansha Scientific), p. 182). Evaluation of the angle of repose and fluidity are an angle of repose of 25~30° provides the best fluidity (measures to prevent arch formation are unnecessary), angle of repose of 31~35° provides good fluidity (measures to prevent arch formation are unnecessary), an angle of repose of 36~40° provides somewhat good fluidity (use a vibrator when necessary), an angle of repose of 41~45° provides mediocre fluidity (critical point), an angle of repose of 46~55° provides somewhat inferior fluidity (agitation and vibration are necessary), an angle of repose of 56~65° provides inferior fluidity (agitate more vigorously), and an angle of repose of 66~90° provides the worst fluidity (special devices and technology necessary (excerpt from Car. R. L. Jr., Chemical Engineering, Jan. 18, p. 166, Table II, 1965). Consequently, the drug with "inferior fluidity" in the present Specification shows an angle of repose of 46~90°, but the present invention can also be applied in order to further improve fluidity of a drug with mediocre fluidity or somewhat good fluidity as long as the results of the present invention are not lost.

The term "obtained by spray drying" in the present Specification means the state of the drug alone or the drug together with a pharmaceutically acceptable carrier dissolved in a solvent that is pharmaceutically acceptable, or suspended with the drug or part or all of the carrier dispersed in a solvent and this solution or suspension being sprayed and dried.

There are no special restrictions to the pharmaceutical preparation carrier used in the present invention as long as it is pharmaceutically acceptable and alleviates the bitter taste of the drug, or improves fluidity of the drug, when spray dried with the drug. However, it is preferred that the carrier be capable of alleviating bitter taste and improving fluidity of the drug. Examples of this pharmaceutical preparation carrier are polymer substances, including water insoluble polymers, gastrosoluble polymers, enterosoluble polymers, and wax-like substances, etc. Examples of water-insoluble polymers are water-insoluble cellulose ether, such as ethyl cellulose, Aquacoat (brand name, Asahi Kasei Co., Ltd.), water-insoluble acrylic copolymer, such as ethyl acrylate-methyl methacrylate-trimethyl ammonium chloride ethyl methacrylate copolymer (for instance, brand name: Eudragit RS, Eudragit RS30D, Rohm Co., Ltd.), ethyl acrylate-methyl methacrylate copolymer dispersion (for instance, Eudragit NE30D, Rohm Co., Ltd.), etc., and the like. Gastrosoluble polyvinyl derivatives, such as polyvinyl acetal diethyl aminoacetate, etc., gastrosoluble acrylic copolymers, such as methyl methacrylate-butyl methacrylate-dimethyl aminoethyl methacrylate copolymer (for instance, brand name Eudragit E, Rohm Co., Ltd.), etc., and the like are examples of gastrosoluble polymers. Enterosoluble cellulose derivatives, such as hydroxypropyl methyl cellulose acetate succinate, hydroxypropylmethyl cellulose phthalate, hydroxymethyl ethyl cellulose phthalate, carboxymethyl ethyl cellulose, etc., enterosoluble acrylic acid copolymers, such as methacrylic acid copolymer L (for instance, brand name: Eudragit L, Rohm Co., Ltd.), methacrylic acid copolymer LD (for instance, brand name: Eudragit L30D-55, Rohm Co., Ltd.), and the like are examples of enterosoluble polymers. Solid fats and oils, such as hydrogenated castor oil, hydrogenated coconut oil, tallow, etc., higher fatty acids, such as stearic acid, lauric acid, myristic acid, palmitic acid, etc., and higher alcohols, such as cetyl alcohol, stearyl alcohol, etc., are examples of wax-like substances. Of these, water-insoluble polymers that are not pH dependent are preferred, water-insoluble cellulose ether or water-insoluble acrylic acid copolymer is further preferred, and ethyl cellulose (ideally Aquacoat (brand name): aqueous ethyl cellulose dispersion) or ethyl acrylate-methyl methacrylate-trimethyl ammonium chloride ethyl methacrylate (ideally Eudragit RS30D (brand name)) are particularly preferred. It is preferred that an appropriate plasticizer be added to the pharmaceutical preparation carrier used in the present invention. Triacetin, triethyl citrate, dibutyl sebacate, acetylated monoglyceride, Eudragit NE30D (brand name, Rohm Co., Ltd.), etc., are examples of this plasticizer. The fluidity of a drug that is not bitter tasting can be improved by the present invention. In addition to the above-mentioned polymer substances, such as water-insoluble polymer, gastrosoluble polymer, enterosoluble polymer, etc., and wax-like substances, etc., a water soluble polymer, saccharide, etc., can be used as the above-mentioned carrier in this case. Examples of the water-soluble polymers that can be used as this carrier are hydroxypropyl cellulose, hydroxypropyl methyl cellulose, polyvinyl pyrrolidone, polyvinyl alcohol, etc. Examples of the saccharide are maltose (preferably maltose syrup powder (containing 83% or more of maltose): Japanese Pharmaceutical Excipients, 1998), glucose, maltitol, sorbitol, trehalose, etc. The pharmaceutical preparation carrier is preferably a saccharide, and of these, maltose is preferred.

The amount of pharmaceutical preparation carrier that is used in the present invention can be adjusted as needed based on how bitter the drug tastes or its fluidity, but it is usually 0.05~3 parts by weight, preferably 0.1~1 part by weight, particularly 0.2 to 1 part by weight, per 1 part by weight drug. When the drug is famotidine, it is 0.2~1 part by weight, preferably 0.3~0.5 part by weight, per 1 part by weight famotidine.

There are no special restrictions to the saccharide base of the quick disintegrating tablet in buccal cavity used in the present invention as long as it is pharmaceutically acceptable. A sugar or sugar alcohol is an example of said saccharide. Lactose, glucose, sucrose, maltose (preferably maltose syrup powder (containing 83% of more of maltose)), trehalose, lactosucrose, etc., are examples of this sugar. Examples of this sugar alcohol are mannitol, xylitol, maltitol, sorbitol, erythritol, etc. One or a combination of 2 or more saccharides can be used. Moreover, this saccharide is preferably used as the granulation product obtained by spraying to coat and/or granulate a "saccharide of low moldability" using a "saccharide of high moldability" as the binder solution when classified in the categories for "saccharide of low moldability" and "saccharide of high moldability" defined in World Early Disclosure Pamphlet WO 95/20380 (corresponds to U.S. Pat. No. 5,576,014).

The term "moldability" in the present Specification in this case means the ability to retain shape when compression molded. The criterion is tablets having a hardness of 0~2 kp for "saccharides of low moldability" and tablets having a hardness of 2 kp or higher for "saccharides of high moldability" when, for instance, 150 mg saccharide have been tableted under a tableting pressure of 10~50 kg/cm$^2$ using a punch with a diameter of 8 mm.

There are no special restrictions to the "saccharide of low moldability" used in the present invention as long as it is pharmaceutically acceptable and has low moldability but will dissolve in the mouth quickly. Examples of said saccharide are lactose, mannitol, glucose, sucrose, xylitol, erythritol, etc., but lactose and mannitol are preferred. One or a combination of two or more of theses saccharides can be used. There are no special restrictions to the amount of saccharide that is added as long as it is an amount that will disintegrate and dissolve in the mouth quickly as a quick disintegrating tablet in buccal cavity of the present invention. Moreover, this amount added is adjusted as needed based on the dose of the drug or the size of the tablet and is usually 30~95 wt/wt %, preferably 50~90 wt/wt %.

There are no special restrictions to the "saccharide of high moldability" used in the present invention as long as it is pharmaceutically acceptable and it has molding strength to such an extent that it can retain its shape when molded into the quick disintegrating tablet in buccal cavity of the present invention. Examples of this saccharide are maltose, maltitol, sorbitol, trehalose, lactosucrose, etc., and maltose and maltitol are preferred. One or a combination of two or more of these saccharides can be used. The amount of these saccharides is usually 1~25 wt/wt %, preferably 2~20 wt/wt %, per the "saccharide of low moldability," or 2~20 wt/wt % of the total preparation.

Various fillers that are pharmaceutically acceptable and are used as additives can also be added to the quick disintegrating tablet in buccal cavity of the present invention. Examples of these fillers are diluent (extender), disintegrant, binder, sour flavoring, foaming agent, artificial sweetener, fragrance, lubricant, coloration agent, stabilizer, etc. One or a combination of 2 or more of these drug fillers are used.

Examples of disintegrants are starches such as corn starch, etc., carmellose calcium, partly pregelatimized starch, crospovidone, lower substituted hydroxypropyl cellulose, etc. Examples of binders are polyvinyl pyrrolidone, hydroxypropyl methyl cellulose, hydroxypropyl cellulose, gum arabic powder, gelatin, pullulan, etc. Examples of sour flavorings are citric acid, tartaric acid, malic acid, etc. Examples of foaming agents are sodium bicarbonate, etc. Examples of artificial sweeteners are saccharine sodium, disodium glycyrrhizinate, aspartame, stevia, sormatin, etc. Examples of fragrances are lemon, lemon-lime, orange, menthol, etc. Examples of lubricants are magnesium stearate, calcium stearate, sucrose fatty acid ester, polyethylene glycol, talc, stearic acid, etc. Examples of coloration agents are food coloring, such as yellow food dye No. 5, red food dye No. 2, blue food dye No. 2, etc.; food lake coloring; iron oxide red, etc. Stabilizers are selected by drug after performing various tests. One or a combination of 2 or more of these additives can be added in an appropriate amount as needed.

The drug-containing particles obtained by spray drying of the present invention are made into a pharmaceutical preparation in the form of a quick disintegrating tablet in buccal cavity. Quick disintegrating tablets in buccal cavity made in accordance with the following conventional manufacturing methods are examples of this tablet:

WO 93/12769 (corresponds to U.S. Pat. No. 5,466,464; drug and saccharide suspended in aqueous agar solution and dried and solidified), WO 95/20380 (corresponds to U.S. Pat. No. 5,576,014), WO 99/47124 (corresponds to European Patent No. EP 1072256), Kokai Patent No. Hei 11(1999)-35451 (mixture of drug, saccharide, and low-melting-point substance tableted under low pressure and then heated and allowed to cool), EP 553777 (corresponds to U.S. Pat. No. 5,501,861, corresponds to U.S. Pat. No. 5,720,974, corresponds to Japanese Kokai Patent No. Hei 05(1993)-271054 (mixture of drug, saccharide and enough water to moisten surface of particles tableted and dried), Japanese Kokai Patent No. Hei 08(1996)-291051 (mixture of drug, water-soluble binder, and water-soluble filler molded under low pressure and then moistened and dried), U.S. Pat. No. 5,223,264 (corresponds to Patent WO 91/04757, corresponds to Japanese National Publication No. Hei 05(1993)-500956) (mixture consisting of drug and foaming component compression molded), EP996424 (corresponds to Japanese Kokai Patent No. Hei 11(1999)-043429) (mixture consisting of drug, sugar alcohol, and L-HPC compression molded).

The method of manufacturing the quick disintegrating tablet in buccal cavity of the present invention will now be described:

The method of manufacturing the quick disintegrating tablet in buccal cavity of the present invention comprises:
(a) the process whereby a bitter tasting drug and/or a drug of inferior fluidity and a pharmaceutical preparation carrier are dissolved and suspended to approximately 30~approximately 70 w/w % in terms of solid concentration in a solvent that is pharmaceutically acceptable to prepare a suspension for spray drying,
(b) the process whereby the suspension obtained in process (a) is spray dried using a rotating disk-type spray dryer to prepare the drug-containing particles, and
(c) the process whereby the drug-containing particles obtained in process (b) and a saccharide are mixed and this mixture is molded (preferably the process whereby a granulation product is prepared by spraying to coat and/or granulate a saccharide of low moldability using a saccharide of high moldability as the binder and this granulation product consisting of saccharides is used as the saccharide, or the process whereby molding obtained by molding under at least the pressure needed to retain tablet form in (c) is (d) further moistened and dried.)

The characterizing point of the method of manufacturing a quick disintegrating tablet in buccal cavity of the present invention is the combination of 1) the use of a liquid wherein a bitter tasting drug and/or a drug of inferior fluidity and a pharmaceutical preparation carrier (preferably containing water-insoluble polymer, particularly at least aqueous ethyl cellulose suspension (preferably containing a plasticizer)) are dissolved and suspended to a high concentration (approximately 30~approximately 70 w/w %, preferably approximately 40~approximately 70 w/w %, particularly approximately 50 to approximately 65 w/w %) in terms of solid concentration in a solvent that is pharmaceutically acceptable and (2) spray drying of the suspension in (1) using a rotating disk-type spray dryer, with the disk operating at low speed (approximately 5,000 to approximately 15,000 rpm, preferably approximately 6,000 to approximately 12,000 rpm). The quick disintegrating tablet in buccal cavity that is manufactured using the characterizing point of this manufacturing method has excellent effects in that bitter taste is thoroughly masked, it has the ability to quickly disintegrate and dissolve in the buccal cavity, and it has the tablet strength needed for good industrial productivity and handling.

Process (a) Preparation of Suspension

There are no particular restrictions as long as it is a method of preparing the suspension for spray drying by dissolving and suspending the bitter tasting drug and/or drug of inferior fluidity and pharmaceutical preparation carrier in a solvent that is pharmaceutically acceptable. There are no special restrictions to the solvent used here as long as it is a solvent that is pharmaceutically acceptable. Examples of this solvent are water, organic solvents, etc. Alcohols (for instance, methanol, ethanol, propanol, isopropanol, etc.), halogenated alkanes (for instance, dichloromethane, chloroform, chloroethane, trichloroethane, carbon tetrachloride, etc.), ketones (for instance, acetone, methyl ethyl ketone, etc.), nitriles (for instance, acetonitrile, etc.), hydrocarbons (for instance, n-hexane, cyclohexane, etc.), etc., are examples of organic solvents. One or a mixture of 2 or more of these organic solvents at the desired ratio can be used, and a mixture with an appropriate percentage of water can also be used. Of these solvents, there is the fear that organic solvent will remain in the pharmaceutical preparation when an organic solvent is used and therefore, of these, water and alcohols are preferred and water is particularly preferred. The dissolved and suspended product can be prepared by conventional methods. The mixer method using a propeller agitating device, a turbine agitating device, etc., the colloid mill method, the homogenizer method, the ultrasonic wave irradiation method, etc., are examples of this method. The solid concentration of the dissolved and suspended product is within the range with which spray drying is possible, that is, approximately 30~approximately 70 w/w %, preferably approximately 40~approximately 70 w/w %, particularly approximately 50~approximately 65 w/w %. In this case, the particle diameter will be smaller and it will not be possible to thoroughly mask bitter taste if the solid concentration is below the lower limit, while the spraying liquid will clog the transfer tubing, making spray drying impossible if the solid concentration is above the upper limit. The pharmaceutical preparation carrier used in the present invention is as previously listed, but water-insoluble cellulose ether or water-insoluble acrylic acid copolymer is preferred, and ethyl cellulose (ideally Aquacoat (brand name): aqueous ethyl cellulose dispersion) or ethyl acrylate-methyl methacrylate-trimethyl ammonium chloride ethyl methacrylate copolymer (ideally Eudragit RS30D (brand name)) is particularly preferred. It is preferred that plasticizer be added as needed to the pharmaceutical preparation carrier used in the present invention.

Process (b) Spray Drying Process

The suspension obtained in process (a) is sprayed into a drying chamber of a spray dryer using a nozzle to evaporate the water or organic solvent in the atomized liquid droplets in a very short period of time. The nozzle can be a 2-fluid nozzle, a multi-fluid nozzle, a pressure nozzle, a rotating disk nozzle, etc. Of these, the rotating disk nozzle is preferred. There are no special restrictions to the conditions as long as they are conditions under which the dissolved and suspended product that was prepared as previously described is sprayed. Moreover, these conditions can be selected as needed in accordance with the individual drug particle pharmaceutical preparation and spray dryer that is used. For instance, air intake temperature is adjusted as needed based on the solvent that is used, but when it is an aqueous system, it is usually 70~200° C., preferably approximately 80~150° C. The amount of liquid sprayed is adjusted as needed based on the scale of the equipment, but for instance, on a laboratory scale (chamber diameter of 0.8 m) level it is usually 10~50 g/min, preferably 20~40 g/min, and on a commercial production scale (chamber diameter of 3.2 m) level it is usually 0.5~2 kg/min, preferably 0.6~1.2 kg/min. The number of turns of the disk of the rotating disk is particularly important in relation to the solid concentration when manufacturing drug-containing particles with a specific mean particle diameter of the present invention. The number of turns of this rotating disk depends on particle diameter of the drug-containing particles that are to be made, but it is usually approximately 5,000~approximately 15,000 rpm, preferably approximately 6,000~approximately 12,000 rpm. When necessary, it is possible to heat the drug-containing particles and thoroughly remove the water or solvent in the drug-containing particles under reduced pressure. There are no special restrictions to mean particle diameter of the drug-containing particles of the present invention as long as the gritty feeling in the buccal cavity is alleviated, but is usually a mean particle diameter of approximately 50~approximately 250 μm, preferably approximately 50~approximately 150 μm.

Process (c) Mixing and Molding Process

There are no particular restrictions as long as it is the process whereby drug-containing particles obtained in process (b) and saccharide are mixed by conventional methods and further "molded" by conventional methods. For instance, A v-type mixing equipment, DC mixing equipment, etc., can be used for this mixing.

There are no special restrictions to the "molding" of the present invention as long as it is the process whereby the shape of a tablet, etc., is made under at least the minimum pressure needed to retain the desired shape. Said "molding" can be performed using, for instance, a conventional tableting machine, such as a single tableting machine or a rotary tableting machine. Tableting pressure at this time is usually 25~800 kg/punch, preferably 50~500 kg/punch, particularly 100~300 kg/punch. If tableting is performed at a pressure lower than this pressure, "cracks" and "defects" will be made in the tablets themselves, or they will "crumble" when transported to the next process of moistening and drying. Moreover, if tableting is performed at a pressure exceeding this pressure, tablet hardness of the tablet itself will be higher than necessary, and therefore, it will not quickly disintegrate in the buccal cavity.

The saccharides used in the present invention are preferably employed as a granulation product obtained by spraying to coat and/or granulate a "saccharide of low moldability" using a "saccharide of high moldability" as the binder. In this case, granulation can be performed by a variety of granulation methods, including fluidized bed granulation, agitation granulation, tumbling granulation, tumbling flow granulation, etc. Of these, fluidized bed granulation is preferred. Examples of embodiments of this process are the process whereby a "saccharide of high moldability" dissolved or suspended in a pharmaceutically acceptable solvent, such as water, alcohol, etc., is sprayed as binder from a 2-fluid nozzle, etc., to coat and/or granulate a mixture of drug-containing particles and "saccharide of low moldability" and thereby obtain a granulation product and this is then mixed with lubricant and "molded," the process whereby as described above, a "saccharide of high moldability" is sprayed as binder to coat and/or granulate a "saccharide of low moldability" and thereby obtain a granulation product and this granulation product is mixed with drug-containing particles and lubricant and then "molded," etc. The amount of "saccharide of high moldability" added at this time is usually 1~25 wt/wt %, preferably 2~20 wt/wt %, per drug obtained by spray drying and/or "saccharide of low moldability," or 2~20 wt/wt % of the entire pharmaceutical preparation.

Process (d) Moistening and Drying Process

The "moistening" of the present invention is the process by means of which strength of the molding obtained by process (c) (tablet) is improved when it is conducted in combination with the drying process, which is the process that follows the moistening process. This "moistening" is determined by the apparent critical relative humidity of the mixture comprising the drug-containing particles, saccharide of low moldability and saccharide of high moldability, but moistening is usually performed to the critical relative humidity of this mixture or higher. For instance, humidity is 30 to 100% RH, preferably 50 to 90% RH. Temperature at this time is 15~50° C., preferably 20~40° C. Treatment time is 1~36 hours, preferably 12~24 hours.

There are no special restrictions to the "drying" in the present invention as long as it is a process by means of which the water content that has been absorbed with moistening is removed. Said "drying" is usually performed at 10~100° C., preferably 20~60° C., particularly 25~40° C. Treatment time is 0.5~5 hours, preferably 1~3 hours.

Various pharmaceutically acceptable fillers, such as disintegrants, stabilizers, binders, diluents, lubricant, etc., can be added during any of the processes involved in conversion to a pharmaceutical preparation of the method of manufacturing a quick disintegrating tablet in buccal cavity of the present invention.

DESCRIPTION OF THE PREFERRED EMBODIMENTS

The present invention will now be explained in further detail while referring to examples, but the present invention is not limited to these examples.

Evaluation Methods

The methods for evaluating the quick disintegrating tablet in buccal cavity of the present invention are described below:

[Hardness tests] Determinations are performed using a Schleuniger tablet hardness meter (Schleuniger Co., Ltd.). The tests are performed with 5 tablets and the mean value is shown. Tablet hardness is represented by the force needed to crush the tablet (units kp). A larger number indicates a stronger tablet.

[Disintegration in buccal cavity tests] Healthy adult males place the tablet of the present invention inside their buccal cavity without having any water inside their mouth and the time until the tablet is completely disintegrated and dissolved by saliva only is determined.

[Fluidity evaluation: angle of repose determination] A funnel for pouring powder is placed above a table for determination of the angle of repose. The angle formed by the surface of a layer of accumulated powder and a horizontal plane when the powder is poured so that none remains in the funnel is determined and this angle (°) serves as the angle of repose. Furthermore, a vibrator can also be used if the pouring operation proves difficult because of inferior fluidity. A larger angle of repose indicates inferior fluidity.

Test 1

The inventors intended to determine the angle of repose of famotidine undiluted powder (bitter tasting drug of inferior fluidity) by the fixed base cone method, but the famotidine was very cohesive and therefore, it could not be fed by funnel or sieve and the angle of repose could not be determined. Consequently, it was judged that the famotidine undiluted powder is an undiluted powder with extremely inferior fluidity. In contrast to this, the angle of repose of famotidine particles that are obtained by spray drying (1,500 g famotidine, 2,000 g Aquacoat (brand name, Asahi Kasei), 150 g Triacetin, and 700 g purified water were mixed to prepare a suspension and this suspension was then spray dried with a spray dryer (Okawara MFG. Co., Ltd., L-8) under a spraying rate of 30 g/min, inlet temperature of 120° C. and disk rotating speed of 8000 rpm (mean particle diameter of 91 μm)) was 36o by the fixed base cone method when fed with a funnel, showing very good fluidity.

EXAMPLE 1

A suspension was prepared by mixing 1,500 g famotidine, 2,000 g Aquacoat (brand name, Asahi Kasei) (aqueous 30 w/w % ethyl cellulose dispersion), 150 g Triacetin, and 700 g purified water to obtain a solid concentration of 52 w/w %. This suspension was spray dried in a spray dryer (Okawara MFG. Co., Ltd. L-8) under a spraying rate of 30 g/min, an inlet temperature of 120° C., and a disk rotating speed of 8,000 rpm to obtain famotidine particles whose bitterness was masked. The famotidine particles had a mean particle diameter at this time of 91 μm and an apparent specific gravity of 0.56 g/ml. Separately, 4,578.6 g mannitol (Towa Kasei), 60 g aspartame (Ajinomoto), and 165.2 g peppermint flavor powder (T. Hasegawa Co., Ltd.) were granulated with an aqueous 15% w/w solution comprising 244.2 g maltose syrup powder (Hayashibara Co., Ltd.; brand name: Sunmalt S) in a fluidized bed granulating machine (Freund Industrial Co., Ltd, FLO-5). After mixing 574.8 g famotidine particles that were obtained and 40 g calcium stearate with 3,385.2 g of this granulated product, 200 mg tablets (8.5 mm in diameter) comprising 20 mg famotidine per 1 tablet were produced using a rotary tableting machine (tablet hardness of 1.1 kp (n=5)). Next, the tablets were kept for 24 hours while heating and moistening at 25° C. and 70% RH using a thermostatic chamber at constant humidity (Tabaiespec Co., Ltd., PR-35C). Then the quick disintegrating tablet in buccal cavity of the present invention was obtained by drying for 3 hours at 30° C. and 40% RH. The tablets that were obtained had a hardness of 5.5 kp (n=10) and oral disintegration time of 15 seconds (n=3). Moreover, the result of dissolution tests on the tablets that were obtained was D 20 min=75.9% (paddle method, 50 rpm, test solution: 900 ml water).

EXAMPLE 2

A suspension was prepared by mixing 900 g famotidine, 900 g Aquacoat, and 600 g Eudragit NE30D (brand name, Rohm Co., Ltd.) to obtain a solid concentration of 56 w/w %. This suspension was spray dried in a spray dryer (Okawara MFG. Co., Ltd., L-8) under a spraying rate of 30 g/min, an inlet temperature of 120° C., and a disk rotating rate of 8,000 rpm to obtain famotidine particles whose bitterness was masked. The famotidine particles had a mean particle diameter of 80 μm, an apparent specific gravity of 0.47 g/ml, and angle of repose of 30° at this time. Separately, 4,593.6 g mannitol, 45 g aspartame, and 165.2 g peppermint flavor powder (T. Hasegawa Co., Ltd.) were granulated with an aqueous 15% w/w solution comprising 244.2 g maltose syrup powder (Hayashibara Co., Ltd.; brand name: Sunmalt S) in a fluidized bed granulating machine (Freund Industrial Co., Ltd, FLO-5). After mixing 427.3 g famotidine particles that were obtained and 27.8 g calcium stearate with 2,324.9 g of this granulated product, 200 mg tablets (diameter of 8.5 mm) comprising 20 mg famotidine per 1 tablet were produced using a rotary tableting machine (tablet hardness of 1.2 kp (n=5)). Next, the tablets were kept for 24 hours while heating and moistening at 25° C. and 70% RH using a thermostatic chamber at constant humidity (Tabaiespec Co., Ltd., PR-35C). Then the quick disintegrating tablet in buccal cavity of the present invention was obtained by drying for 3 hours at 30° C. and 40% RH. The tablets that were obtained had a hardness of 6.4 kp (n=10) and oral disintegration time of 20 seconds (n=3). Moreover, the result of dissolution tests on the tablets that were obtained was D 20 min=75.2% (paddle method, 50 rpm, test solution: 900 ml water).

EXAMPLE 3

A suspension was prepared by mixing 100 g famotidine, 133.3 g Aquacoat, 10 g acetylated monoglyceride (Myvacent) and 25 g purified water to obtain a solid concentration of 56 w/w %. This suspension was spray dried in a spray dryer (Okawara MFG. Co., Ltd., L-8) under a spraying rate of 30 g/min, an inlet temperature of 120° C., and a disk rotating speed of 6,000 rpm to obtain famotidine particles whose bitterness was masked. The famotidine particles had a mean particle diameter of 123 μm, an apparent specific gravity of 0.74 g/ml, and angle of repose of 38° at this time. Separately, 791.8 g mannitol were granulated with an aqueous 15% w/w solution comprising 40 g maltose syrup powder (Hayashibara Co., Ltd.; brand name: Sunmalt S) in a fluidized bed granulating machine (Okawara MFG. Co., Ltd., UNI-GLATT).

After mixing 30 g famotidine particles that were obtained, 1.65 g peppermint flavor (T. Hasegawa Co., Ltd.), and 2 g calcium stearate with 166.4 g of this granulation product, 200 mg tablets (diameter of 8.5 mm) comprising 20 mg famotidine per 1 tablet were produced using a rotary tableting machine (tablet hardness of 1.1 kp (n=5)). Next, the tablets were kept for 24 hours while heating and moistening at 25° C. and 70% RH using a thermostatic chamber at constant humidity (Tabaiespec Co., Ltd., PR-35C). Then the quick disintegrating tablet in buccal cavity of the present invention was obtained by drying for 3 hours at 30° C. and 40% RH. The tablets that were obtained had a hardness of 3.1 kp (n=5) and oral disintegration time of 15 seconds (n=3).

Test 2: Taste Test

A taste test was conducted by 33 people on the product of the present invention and a disintegrating tablet in buccal cavity comprising famotidine whose bitter taste had not been masked as the comparative product. The results are listed in Table 1. After multiplying the score by the number of people using the following scores, bitter taste was evaluated as the mean score. The evaluation scores for bitter taste are almost no bitter taste noted: 0, slight bitter taste noted: 1, strong bitter taste noted: 3. When the mean score is less than 1, bitter taste poses no problems in terms of taking the product, while if the mean score is 1 or higher, taking the product is avoided because of its bitter taste. As a result of the test, few people noticed the bitter taste, with the mean score being 1 or less, indicating that the product of the present invention is a good disintegrating tablet in buccal cavity with which bitterness of famotidine is sufficiently alleviated.

TABLE 1

TASTE SCORE EVALUATION

| | Pharmaceutical preparation of present invention | | Comparative pharmaceutical preparation | |
|---|---|---|---|---|
| | Number of people | Score | Number of people | Score |
| No bitter taste | 26 people | 0 | 5 people | 0 |
| Slight bitter taste | 7 people | 7 | 22 people | 22 |
| Strong bitter taste | 0 people | 0 | 6 people | 18 |
| Mean score overall evaluation | | 0.2 | | 1.2 |

Score: Strong bitter taste (3 points), slight bitter taste (1 point), No bitter taste (0 point) [out of 33 people]

EXAMPLE 4

A suspension was prepared by mixing 600 g acetaminophen (bitter tasting drug of inferior fluidity), 640 g Aquacoat, and 48 g Triacetin to obtain a solid concentration of 65 w/w %. This suspension was spray dried in a spray dryer (Okawara MFG. Co., Ltd., L-8) under a spraying rate of 15.5 g/min, an inlet temperature of 120° C., and a disk rotating speed of 10,000 rpm to obtain acetaminophen particles whose bitterness was masked. The acetaminophen particles had a mean particle diameter of 96 μm, an apparent specific gravity of 0.62 g/ml, and angle of repose of 34o at this time. Then 250 g of these acetaminophen particles, 74.8 g mannitol, and 90.0 g lactose were granulated with an aqueous 15% w/w solution comprising 22.5 g maltose syrup powder (Hayashibara Co., Ltd.; brand name: Sunmalt S) in a fluidized bed granulating machine (Okawara MFG. Co., Ltd., UNI-GLATT).

After mixing 1.4 g peppermint flavor (T. Hasegawa Co., Ltd.), 9.0 g aspartame, and 2.3 g magnesium stearate with this granulation product, 450 mg tablets (diameter of 11 mm) per 1 tablet were produced using a rotary tableting machine (tablet hardness of 1.7 kp (n=5)). Next, the tablets were kept for 24 hours while heating and moistening at 25° C. and 70% RH using a thermostatic chamber at constant humidity (Tabaiespec Co., Ltd., PR-35C). Then the quick disintegrating tablet in buccal cavity of the present invention was obtained by drying for 3 hours at 30° C. and 40% RH. The tablets that were obtained had a hardness of 5.8 kp (n=5) and oral disintegration time of 20 seconds (n=3).

Test 3: Property Evaluation Tests of Spray Dried Particles

The properties of spray dried particles prepared with various contents and under various manufacturing conditions are shown in Table 2. Preparation was with the Okawara MFG. Co., Ltd. L-8 spray dryer.

TABLE 2

|  | A-1 | A-2 |  | C-1 | C-2 |
|---|---|---|---|---|---|
| Acetaminophen | 600 | 600 | Calcium carbonate | 600 | 600 |
| Aquacoat | 640 | 640 | Maltose syrup powder | 60 | 60 |
| Triacetin | 48 | 48 |  |  |  |
| Solid concentration (w/w %) | 65 | 65 | Solid concentration (w/w %) | 60 | 60 |
| <Operating conditions> |  |  | <Operating conditions> |  |  |
| Spraying rate g/min | 15.5 | 14.0 | Spraying rate g/min | 42 | 42 |
| Inlet temperature ° C. | 120 | 120 | Inlet temperature ° C. | 120 | 120 |
| Disk rotating speed rpm | 10000 | 15000 | Disk rotating speed rpm | 10000 | 8000 |
| <Particle properties> |  |  | <Particle properties> |  |  |
| Mean particle diameter μm | 96 | 93 | Mean particle diameter μm | 62 | 69 |
| Apparent specific gravity g/ml | 0.62 | 0.63 | Apparent specific gravity g/ml | 1.15 | 1.198 |
| Angle of repose ° | 34 | 36 | Angle of repose ° | 36 | 34 |

EXAMPLE 5

The inventors intended to determine the angle of repose of calcium carbonate undiluted powder (drug of inferior fluidity) (Nitto Funka Kogyo K. K.) by the fixed base cone method, but the calcium carbonate was very cohesive and therefore, it could not be fed by funnel. As a result of determination that was then performed with a vibrator, the angle of repose was 50°, indicating that fluidity was not good.

A suspension was prepared by mixing 600 g calcium carbonate, 60 g maltose syrup powder, and 440 g purified water to obtain a solid concentration of 60 w/w %. This suspension was spray dried in a spray dryer (Okawara MFG. Co., Ltd., L-8) at a spray rate of 42 g/min, inlet temperature of 120° C., and disk rotating speed of 8,000 rpm to obtain calcium carbonate particles of improved fluidity. The calcium carbonate particles had a mean particle diameter of 69 μm, apparent specific gravity of 1.18 g/ml, and angle of repose of 34o at this time. 220 g of these calcium carbonate particles and 276.4 g mannitol were granulated with an aqueous 15 w/w % solution comprising 26 g maltose syrup powder (Hayashibara Co., Ltd.; brand name Sunmalt S) in a fluidized bed granulating machine (Okawara MFG. Co., Ltd., UNI-GLATT).

After mixing 2.6 g magnesium stearate with this granulation product, tablets (11 mm in diameter) of 525 mg per 1 tablet were manufactured using a rotary tableting machine (tablet hardness of 1.9 kp (n=5)). Next, these tablets were kept for 24 hours while heating and moistening at 25° C. and 70% RH using a thermostatic chamber at constant humidity (Tabaiespec Co., Ltd., PR-35C). Then they were dried for 3 hours at 30° C. and 40% RH to obtain the quick disintegrating tablet in buccal cavity of the present invention. The tablets that were obtained had a hardness of 6.1 kp (n=5) and an oral disintegration time of 25 seconds (n=3).

(Results and Discussion)

Particles with excellent fluidity, whether acetaminophen particles or calcium carbonate particles, were obtained from various contents and under various manufacturing conditions. Moreover, apparent specific gravity was approximately 0.6 and approximately 1.2, respectively, confirming that they were compact particles.

Test 4: Test Relating to Solid Concentration

A suspension was prepared by mixing 300 g famotidine, 140 g Aquacoat, and 60 g Endragitr NE30D to obtain a solid concentration of 72 w/w %. However, fluidity of the liquid was inferior and it was considered that it would be impossible to feed the liquid to the spray dryer and therefore, a suspension was prepared by adding 53.8 g purified water to obtain a solid concentration of 65 w/w %. This suspension was spray dried at a spraying rate of 30 g/min, inlet temperature of 120° C., and disk rotating speed of 6,000 rpm using a spray dryer (Okawara MFG. Co., Ltd., L-8) to obtain famotidine particles whose bitter taste had been masked. The famotidine particles had a mean particle diameter of 171 μm at this time.

Next, a suspension was prepared by mixing 50 g famotidine, 53.3 g Aquacoat, 4 g Triacetin, and 242.7 g purified water to obtain a solid concentration of 20 w/w % This suspension was spray dried in a spray dryer (OKAWARA MFG. CO. LTD., L-8) under spraying rate of 24 g/inin, an inlet temperature of 150° C., and a disk rotating speed of 8,000 rpm to obtain famotidine particles. When the particles were taken in buccal, they gave the strong bitter taste. The famotidine particles had a mean particle diameter of 99 um and an apparent specific gravity of 0.40 g/ml.

(Discussion)

It is difficult to feed the suspension when the solid concentration is 72 w/w %, in the case of famotidine, particularly famotidine of needle-shaped crystal, but when the solid concentration is 65 w/w %, these suspensions can be fed and therefore, it appears that the upper limit in terms of solid concentration is approximately 70 w/w %.

Moreover, the particles obtained by the spray drying of a low solid concentration (20 w/w %) had the large particle diameter, but could not be masked the bitter taste. It is considered that the particles might be hollow predicted by the fact that the apparent specific gravity of the particles was low. This led to increase the surface area of particles and show the bitter taste. Therefore it is concluded that high solid concentration of the suspension for spray drying is necessary to obtain the particles whose bitter taste can be thoroughly masked.

EXAMPLE 6

The inventor intended to determine the angle of repose of amboxol hydrochloride (bitter tasting drug of inferior fluidity) by the fixed base cone method, but the amboxol hydrochloride was very cohesive and therefore, it could not be fed by funnel. And it also could not be fed by funnel even using the vibrator.

A suspension was prepared by mixing 300 g ambroxol hydrochloride, 320 g Eudragit RS30D, 24 g Triacetin, and 106 g purified water to obtain a solid concentration of 56 w/w %. This suspension was spray dried in a stray dryer (OKAWARA MFG. CO., LTD., L8) under spraying rate of 30 g/min, an inlet temperature of 120° C., and a disk rotating speed of 8000 rpm to obtain ambroxol hydrochloride particles whose bitterness was masked. The ambroxol hydrochloride particles had a mean particle diameter of 89 um, an apparent specific gravity of 0.78 g/ml and angle of repose of 32. Then 42 g of these ambroxol hydrochloride particles and 336 g of mannitol were granulated with an aqueous 15% w/w % solution comprising 20 g maltose syrup powder (Hayashibara Co. Ltd.; brand name Sunmalt S) in a fluidized bed granulating machine (OKAWARA MFG. CO., LTD., UNI-GLATT).

After mixing 1.5 g magnesium stearate with 298.5 g of this granulation product, 200 mg tablets (diameter of 8.5 mm) comprising 15 mg ambroxol hydrochloride per 1 tablet were produced using rotary tableting machine (tablet hardness of 1.9 kp(n=5)). Next, the tablets were kept for 24 hours while heating and moistening at 25 C and 70% RH using a thermostatic chamber at constant humidity (Tabaiespec Co., Ltd., PR-35C). Then the quick disintegrating tablet in buccal cavity of the present invention was obtained by drying for 3 hours at 30 C and 40% RH. The tablets that were obtained had a hardness of 3.3 kp (n=5) and oral disintegration time of 12 seconds (n=3).

INDUSTRIAL APPLICABILITY

The quick disintegrating tablet in buccal cavity of the present invention is characterized in that drug-containing particles consisting of bitter tasting drug and/or drug of inferior fluidity and a pharmaceutical preparation carrier and having a specific mean particle diameter (approximately 50~approximately 250 µm, preferably approximately 50~approximately 150 µm) and an apparent specific specific gravity (approximately 0.5~approximately 1.2, preferably approximately 0.5~approximately 1) are added. The bitter taste of a bitter tasting drug can be alleviated and fluidity of a drug (preferably a drug of needle-shaped crystal) can be improved, and the bitter taste of a bitter tasting drug of inferior fluidity can be alleviated and fluidity can be improved by these drug-containing particles and quick disintegrating tablets in buccal cavity containing these particles. Moreover, the present invention presents a quick disintegrating tablet in buccal cavity with which the bitter taste of a bitter tasting drug with needle-shaped crystal in particular is masked and fluidity is improved without reducing bioavailability and there is no sense of extraneous matter when this drug is used in quick disintegrating tablet in buccal cavity and unwanted drug elution does not occur, even after tableting. Moreover, in addition to quick disintegrating tablets in buccal cavity, the drug-containing particles of the present invention can also be used for chewable tablets or tablets that are to be dissolved or suspended in water when taken.

Moreover, the drug-containing particles of the present invention are particularly useful because when used for a drug that is bitter tasting and/or reduces fluidity of a granulation product, for instance, a drug of needle-shaped crystal, etc., they will alleviate bitter taste and improve fluidity and further, when used for the manufacture of quick disintegrating tablets in buccal cavity by tableting under low pressure in particular, quick disintegrating tablets in buccal cavity can be manufactured without any damage from tableting.

What is claimed is:

1. A quick disintegrating tablet in buccal cavity, said quick disintegrating tablet comprising:
    a) a plurality of drug-containing particles, wherein each particle comprises a bitter tasting drug and a pharmaceutical preparation carrier, wherein each particle has a mean diameter of approximately 50 to approximately 250 µm and an apparent specific gravity of approximately 0.5 to approximately 1.2, obtained by spray-drying; and
    b) a saccharide.

2. The quick disintegrating tablet in buccal cavity of claim 1, wherein the pharmaceutical preparation carrier is 1 or 2 or more selected from the group consisting of water-insoluble polymers, gastrosoluble polymers, enterosoluble polymers, wax-like substances and saccharides.

3. The quick disintegrating tablet in buccal cavity of claim 2, wherein the pharmaceutical preparation carrier is a water-insoluble polymer.

4. The quick disintegrating tablet in buccal cavity of claim 3, wherein the water-insoluble polymer is a water-insoluble cellulose ether or a water-insoluble acrylic acid copolymer.

5. The quick disintegrating tablet in buccal cavity of claim 1, wherein the amount of pharmaceutical preparation carrier added is about 0.05 to about 3 parts by weight per 1 part by weight bitter tasting drug.

6. The quick disintegrating tablet in buccal cavity of claim 1, wherein the saccharide is a granulation product obtained by spraying to coat and/or granulate a saccharide of low moldability using a saccharide of high moldability as a binder.

7. The quick disintegrating tablet in buccal cavity of claim 6, wherein the saccharide of low moldability is 1 or 2 or more selected from the group consisting of lactose, mannitol, glucose, sucrose, xylitol, and erythritol.

8. The quick disintegrating tablet in buccal cavity of claim 6, wherein the saccharide of high moldability is 1 or 2 or more selected from the group consisting of maltose, maltitol, sorbitol, trehalose, and lactosucrose.

9. The quick disintegrating tablet in buccal cavity of claim 1, wherein the mean particle diameter of the plurality of drug-containing particles is approximately 50 µm to approximately 150 µm.

10. The quick disintegrating tablet in buccal cavity of claim 1, wherein the apparent specific gravity of the plurality of drug-containing particles is approximately 0.5 to approximately 1.

11. A method for manufacturing a quick disintegrating tablet in buccal cavity, said quick disintegrating tablet comprising a drug and a saccharide, said method comprising the steps of:
(a) dissolving a bitter tasting drug and a pharmaceutical preparation carrier to form a mixture that is dissolved and suspended to approximately 30 to approximately 70 w/w % in terms of solid concentration in a solvent that is pharmaceutically acceptable to prepare a suspension for spray drying;
(b) spray drying said suspension using a rotating disk-type spray dryer, with the disk rotating at a speed of approximately 5,000 to approximately 15,000 rpm to prepare the drug-containing particles; and
(c) mixing the drug-containing particles with a saccharide to form a mixture that is molded.

12. The method for manufacturing a quick disintegrating tablet in buccal cavity of claim 11, wherein said saccharide is a granulation product obtained by spraying to coat and/or granulate a saccharide of low moldability using a saccharide of high moldability as a binder.

13. The method for manufacturing a quick disintegrating tablet in buccal cavity of claim 11, wherein (d) the process of moistening and drying is further performed in succession to process (c) on the molding obtained under at least the pressure needed to retain tablet form.

14. The method for manufacturing a quick disintegrating tablet in buccal cavity of claim 11, wherein the solid concentration in step (a) is approximately 40 to approximately 70 w/w %.

15. The method for manufacturing a quick disintegrating tablet in buccal cavity of claim 11, wherein the rotating speed of the rotating disk in process (b) is approximately 6,000 to approximately 12,000 rpm.

16. The method for manufacturing a quick disintegrating tablet in buccal cavity of claim 11, wherein a bitter tasting drug whose particle diameter has been brought to approximately 5 to approximately 100 μm is used in process (a).

17. A quick disintegrating tablet in buccal cavity, which is manufactured by the method of claim 11.

* * * * *